(12) United States Patent
Seo

(10) Patent No.: US 10,603,111 B2
(45) Date of Patent: Mar. 31, 2020

(54) COMPUTER ASSISTANCE SYSTEM AND METHOD FOR IMAGE-GUIDED REDUCTION OF FRACTURE

(71) Applicant: CORELINE SOFT CO., LTD., Seoul (KR)

(72) Inventor: Hyun Gi Seo, Gyeonggi-Do (KR)

(73) Assignee: Coreline Soft Co., Ltd., Seoul (KR)

( * ) Notice: Subject to any disclaimer, the term of this patent is extended or adjusted under 35 U.S.C. 154(b) by 0 days.

(21) Appl. No.: 15/977,064

(22) Filed: May 11, 2018

(65) Prior Publication Data

US 2018/0325599 A1  Nov. 15, 2018

(30) Foreign Application Priority Data

May 12, 2017  (KR) .......................... 10-2017-0059292

(51) Int. Cl.
| | |
|---|---|
| *A61B 34/10* | (2016.01) |
| *G06T 17/20* | (2006.01) |
| *G06T 19/00* | (2011.01) |
| *G06T 7/00* | (2017.01) |
| *G06T 7/33* | (2017.01) |
| *A61B 34/30* | (2016.01) |

(Continued)

(52) U.S. Cl.
CPC ............ *A61B 34/10* (2016.02); *G06T 7/0016* (2013.01); *G06T 7/33* (2017.01); *G06T 17/20* (2013.01); *G06T 19/00* (2013.01); *A61B 34/20* (2016.02); *A61B 34/30* (2016.02); *A61B 2034/105* (2016.02); *A61B 2090/3916* (2016.02); *G06T 2200/24* (2013.01); *G06T 2207/30008* (2013.01); *G06T 2210/41* (2013.01); *G06T 2219/004* (2013.01); *G06T 2219/028* (2013.01)

(58) Field of Classification Search
None
See application file for complete search history.

(56) References Cited

U.S. PATENT DOCUMENTS

| | | | |
|---|---|---|---|
| 5,799,055 | A | 8/1998 | Peshkin et al. |
| 6,069,932 | A | 5/2000 | Peshkin et al. |
| 7,117,027 | B2 | 10/2006 | Zheng et al. |

(Continued)

FOREIGN PATENT DOCUMENTS

| | | |
|---|---|---|
| EP | 3 127 514 A1 | 2/2017 |
| JP | 2016-532475 A | 10/2016 |

(Continued)

*Primary Examiner* — Michelle Chin
(74) *Attorney, Agent, or Firm* — Nelson Mullins Riley & Scarborough LLP; Kongsik Kim

(57) ABSTRACT

Disclosed herein are a computer assistance method for the reduction of a fracture and a computing system for assisting the reduction of a fracture. The computer assistance method includes: generating a first model of a first bone, which is a treatment target, based on a pre-operative medical image; generating a second model, assumed to be obtained after the restoration of the first bone, based on the pre-operative medical image; acquiring a third model in which the spatial information of the first model has been updated by incorporating, into the spatial information, the movement of the first bone occurring during treatment after the installation of markers onto the first bone; and generating overlay visual information based on the second and third models registered onto the same space.

12 Claims, 6 Drawing Sheets

(51) Int. Cl.
 *A61B 34/20* (2016.01)
 *A61B 90/00* (2016.01)

(56) References Cited

U.S. PATENT DOCUMENTS

| | | | |
|---|---|---|---|
| 7,618,419 B2 | 11/2009 | Lavallee | |
| 9,078,710 B2 | 7/2015 | Thoren et al. | |
| 9,554,868 B2 | 1/2017 | Regazzoni | |
| 9,610,101 B2 | 4/2017 | Tang et al. | |
| 2014/0343572 A1* | 11/2014 | Windolf | A61B 17/1703 606/130 |
| 2016/0235381 A1 | 8/2016 | Scanlan et al. | |
| 2016/0331463 A1 | 11/2016 | Notzli et al. | |
| 2016/0331465 A1 | 11/2016 | Kim et al. | |
| 2017/0143494 A1* | 5/2017 | Mahfouz | A61B 34/20 |
| 2017/0165008 A1* | 6/2017 | Finley | G06T 7/74 |

FOREIGN PATENT DOCUMENTS

| | | |
|---|---|---|
| JP | 2017-507689 A | 3/2017 |
| KR | 20030079961 A | 10/2003 |
| KR | 10-0747138 B1 | 8/2007 |
| KR | 10-2015-0115267 | 10/2015 |

\* cited by examiner

COMPUTER ASSISTANCE SYSTEM AND METHOD FOR IMAGE-GUIDED REDUCTION OF FRACTURE

CROSS-REFERENCE TO RELATED APPLICATION

This application claims under 35 U.S.C. § 119(a) the benefit of Korean Patent Application No. 10-2017-0059292 filed on May 12, 2017, which is incorporated herein by reference.

TECHNICAL FIELD

The present invention relates generally to a computer assistance method and system for the image-guided reduction of a fracture, and more specifically to technology which is capable of, when providing guidance on the locations and orientations of a bone during an operation for the reduction of a fracture, providing an intuitive interface and improving user convenience.

BACKGROUND ART

A surgical treatment procedure for a bone fracture occurring in an arm, a leg, a pelvis, or the like includes the reduction and fixation of bone fragments. The fixation of bone fragments is the process of continuously applying force for a long time in order to maintain the reduced state of a broken bone, and is thus a process which is considerably burdensome for a surgeon.

Meanwhile, although the reduction of bone fragments is performed through the assistance of a computer, the registration between medical images and the alignment of twisted fragments are still complex and difficult to handle.

A typical method is to match and align the proximal and distal parts of a broken bone by using a real-time fluoroscopic image. Although this method has been computerized to a considerable extent due to the development of modality capable of acquiring a medical image recently, the decision of a doctor, i.e., an expert, plays an important role.

An example of a computer assistance method for the reduction of a fracture is disclosed in U.S. Pat. No. 7,618,419 entitled "METHOD AND SYSTEM OF COMPUTER ASSISTANCE FOR THE REDUCTION OF A FRACTURE."

This prior art is advantageous in that it can be applied to non-radiographic images, such as ultrasonic images. The prior art proposes a technique of generating a mirror image of an unbroken bone and then using the mirror image as a reference during the reduction of a broken bone.

Although the prior art can improve the process of dislocation efficiently because the proximal and distal parts of the broken bone can be registered based on the mirror image of the unbroken bone, the prior art is still problematic in that the efficiency of the alignment of orientations is low.

SUMMARY OF THE DISCLOSURE

The present invention has been conceived to overcome the above-described problems of the prior art, and an object of the present invention is not only to simply improve the registration between medical images efficiently, but also to provide an improved user interface for guidance on an operation such that a user can clearly become aware of the accurate relative locations, orientations, and alignment of the proximal and distal parts of a broken bone.

An object of the present invention is to provide guidance which is configured to generate a 3D model of a fractured bone from a previously photographed pre-operative image, to register and compare the spatial information of the fractured bone acquired in real time in connection with markers with the existing 3D model, and to provide views of the 3D model in various directions, thereby enabling the accurate reduction of the fractured bone without twisting as well as dislocation and spacing.

Meanwhile, for a site where an operation for the reduction of a fracture is performed, reference may be made to Korean Patent Application Publication No. 10-2015-0115267 entitled "Bone Traction Device and Fracture Reduction Apparatus Including the Same." This patent publication discloses the process of fastening a bone by means of a robot arm and continuously applying traction force to the bone in order to maintain a reduced state. In this process, there is used a control apparatus for controlling a robot (a so-called "surgical navigation system").

An object of the present invention is to provide user guidance which is capable of improving the completeness of a current operation by using a 3D model using a previously generated pre-operative image and a real-time 3D model in which spatial information has been updated at a site where an operation for the reduction of a fracture is performed using a surgical navigation system, etc. Although the accurate performance of an operation via the surgical navigation system in the process basically depends on the precision of the surgical navigation system and a robot and the proficiency of an operator, image-based user guidance designed to transfer information about the status of a current operation and provide feedback regarding whether the reduction of a bone is being accurately performed cannot be achieved by the prior art.

An object of the present invention is to provide a user interface which is capable of constructing a workflow through the image processing of medical images, comparing a 3D model with a 3D model in which current real-time spatial information has been updated through the workflow, and more effectively transferring the results of the comparison to a user (an operator).

Meanwhile, the conventional method for the image-guided reduction of a fracture performs real-time radiography, such as fluoroscopy, even during an operation, and provides image guidance based on an image acquired by photographing an ultrasonic image in real time, as described in U.S. Pat. No. 7,618,419 entitled "METHOD AND SYSTEM OF COMPUTER ASSISTANCE FOR THE REDUCTION OF A FRACTURE." Fluoroscopy is problematic in that the exposure of a patient to radioactive rays increases. In the case of the ultrasonic image, additional manpower is required to acquire an ultrasonic image during an operation, and inconvenience arises in that a space for an operation is limited. An object of the present invention is to provide a 3D model in which real-time spatial information has been updated through location tracking and synchronization regarding markers attached to a leg of a patient without actually photographing/imaging a radiographic or ultrasonic image during an operation, thereby providing intuitive and efficient guidance and an intuitive and efficient user interface to a user (an operator).

According to an aspect of the present invention, there is provided a computing system for assisting the reduction of a fracture, the computing system including a processor and being connected to a display device; wherein the processor including: a first generation unit configured to generate a first model of a first bone, which is a treatment target, based on a pre-operative medical image; a second generation unit configured to generate a second model, assumed to be obtained after the restoration of the first bone, based on the pre-operative medical image; a reception unit configured to receive/acquire the spatial information of the first model. The spatial information of the first model may be updated by incorporating, into the spatial information, the movement of the first bone occurring during treatment after the installation of markers onto the first bone; and a third generation unit configured to generate a third model based on the updated spatial information of the first model, and to generate overlay visual information based on the second and third models registered onto the same space.

The third generation unit may be further configured to match the outline of the first bone represented by the third model with the first portion of the outline of the second model, and to generate the overlay visual information such that a second portion of the outline of the second model, which is the remainder of the outline of the second model, is connected to the outline of the first bone seamlessly.

The third generation unit may be further configured to extract the first central axis of the first bone and the second central axis of the second model, and to generate the overlay visual information such that the second central axis is displayed for a portion where the first bone is missing by matching the first central axis of the first bone with the second central axis of the second model.

The third generation unit may be further configured to generate display information for the proximal segment of the first bone and the distal segment of the first bone to be displayed along with the overlay visual information, and to generate the overlay visual information for the proximal segment of the first bone such that the overlay visual information guides the location of the distal segment relative to the proximal segment.

The third generation unit may be further configured to generate the overlay visual information such that the overlay visual information includes visual information indicating the distance between the proximal segment of the first bone and the distal segment of the first bone. Furthermore, the overlay visual information may include visual information indicating whether the orientations of the central axis of the proximal segment and the central axis of the distal segment match each other.

The third generation unit may be further configured to provide one or more of a rotation view, a lateral view, and an anterior view for the third model, and to generate the overlay visual information based on the second model for each of the one or more views provided for the third model.

The second model may be generated through the symmetric transformation of a second bone located opposite to the first bone. In another embodiment, the second model may be generated using information about a plan for the reduction of a fracture of the first bone. In this case, the second model may be generated based on a standardized anatomical model of the first bone, and may be set as a target model to be restored after an operation.

According to an aspect of the present invention, there is provided a computer assistance method for the reduction of a fracture, the method including: generating a first model of a first bone, which is a treatment target, based on a pre-operative medical image; generating a second model, assumed to be obtained after the restoration of the first bone, based on the pre-operative medical image; acquiring a third model in which the spatial information of the first model has been updated by incorporating, into the spatial information, the movement of the first bone occurring during treatment after the installation of markers onto the first bone; and generating overlay visual information based on the second and third models registered onto the same space.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Embodiments of the present invention will be described in detail below with reference to the accompanying drawings. In the following description of the present invention, when it is determined that a detailed description of a well-known component or function may unnecessarily make the gist of the present invention obscure, the detailed description will be omitted.

The present invention proposes technology for effectively generating and transferring information required to manipulate a robot arm in an environment in which the robot arm can be manipulated using a surgical navigation system and necessary medical image information can be acquired via a monitor, as can be understood from the above-described Korean Patent Application Publication No. 10-2015-0115267 entitled "Bone Traction Device and Fracture Reduction Apparatus Including the Same."

Furthermore, the present invention proposes technology for providing abundant information suitable for the professionalism of a user via a monitor in real time so that an accurate and precise operation can be performed using the professional knowledge and experience of the user when the user manipulates a surgical navigation system.

The process of generating information, supporting an accurate and precise operation, on a monitor according to the present invention is performed via a previously constructed computer-based workflow, and may be implemented via the process of generating a 3D model of an operation target bone in advance via a 3D medical image (example, a CT image, an MRI image, or the like) previously acquired before an operation.

In the environment in which the present invention is used, a user continuously manipulates a surgical navigation system. Accordingly, the environment is assumed to be a situation in which it is not easy for the user to freely interact with displayed information. Therefore, it is required that displayed information should intuitively transfer information about the statue of the progress of an operation and information essential for the decision of a user should be effectively visualized.

Figure 1:
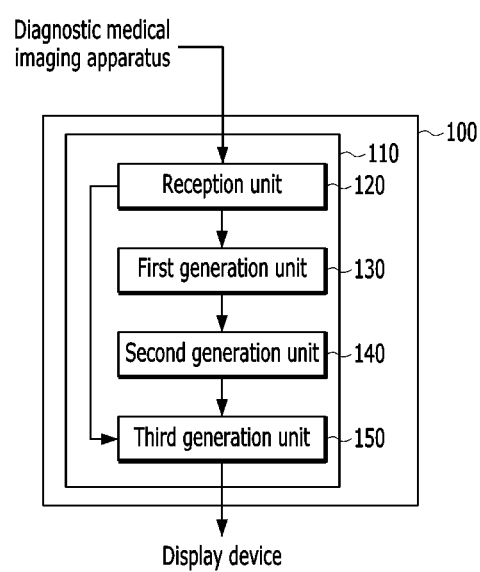
FIG. 1 is a view showing a computing system 100 for assisting the reduction of a fracture according to an embodiment of the present invention.

FIG. 1 is a view showing a computing system 100 for assisting the reduction of a fracture according to an embodiment of the present invention.

The computing system 100 includes a processor 110, and is connected to a display device. The processor 110 includes: a first generation unit 130 configured to generate a first model of a first bone, i.e., a treatment target, based on a pre-operative medical image; a second generation unit 140 configured to generate a second model, assumed to be obtained after the restoration of the first bone, based on the pre-operative medical image; a reception unit 120 configured to receive/acquire the spatial information of the first model which may have been updated by incorporating, into the spatial information, the movement of the first bone occurring during treatment after the installation of markers onto the first bone; and a third generation unit 150 configured to generate a third model based on the updated spatial information of the first model, and to generate overlay visual information based on the second and third models registered onto the same space.

The third generation unit 150 configured to generate overlay visual information plays a key role in the configuration of the computing system 100. The third generation unit 150 may match the outline of the first bone represented by the third model with the first portion of the outline of the second model, and may generate the overlay visual information such that a second portion of the outline of the second model, i.e., the remainder of the outline of the second model, is connected to the outline of the first bone seamlessly.

The third generation unit 150 may extract the first central axis of the first bone and the second central axis of the second model, and may generate the overlay visual information such that the second central axis is displayed for a portion where the first bone is missing by matching the first central axis of the first bone with the second central axis of the second model.

The third generation unit 150 may generate display information for the proximal segment of the first bone and the distal segment of the first bone to be displayed along with the overlay visual information, and may generate the overlay visual information for the segment of the first bone such that the overlay visual information may guide the location of the distal segment relative to the proximal segment.

The third generation unit 150 may generate the overlay visual information such that the overlay visual information includes visual information indicating the distance between the proximal and distal segments of the first bone. Furthermore, the overlay visual information may include visual information indicating whether the orientations of the central axis of the proximal segment and the central axis of the distal segment match each other.

The third generation unit 150 may provide one or more of a rotation view, a lateral view, and an anterior view for the third model, and may generate the overlay visual information based on the second model for each of the one or more views provided for the third model.

The second model may be generated through the symmetric transformation of the second bone located opposite to the first bone. In another embodiment, the second model may be generated using information about a plan for the reduction of a fracture of the first bone. In this case, the second model may be generated based on a standardized anatomical model of the first bone, and may be set as a target model to be restored after an operation.

Figure 2:
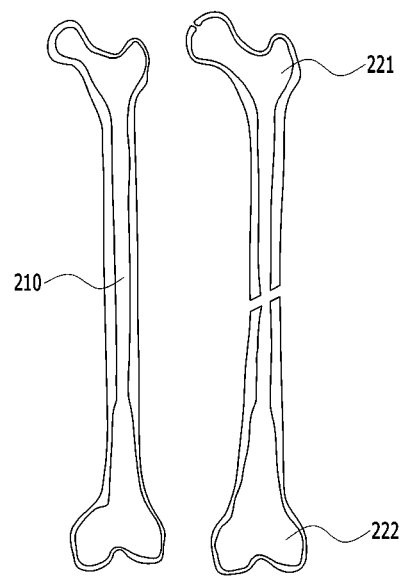
FIG. 2 is a view showing the proximal and distal parts of unbroken and broken bones.

FIG. 2 is a view showing the proximal and distal parts of unbroken and broken bones.

Referring to FIG. 2, a planar image 210 of an unbroken whole bone, a planar image 221 of the proximal part of a broken bone, and a planar image 222 of the distal part of the broken bone are shown. These planar images are formed via the same reference surface, and thus comparisons in size and location may be made. In FIG. 2, in order to help understanding, the planar image 210 of the whole bone is mirrored, and is disposed such that it may be compared with the planar image 221 of the proximal part of the broken bone and the planar image 222 of the distal part of the broken bone at the same position.

After the bone has been segmented in the pre-operative image, a 3D surface model is generated based on the results of the segmentation of the bone. Although the planar image obtained by projecting a 3D surface model onto a single reference surface is introduced in FIG. 2, a 3D surface model may be used to transfer intuitive information to a user during an operation process in another embodiment of the present invention.

Figure 3:
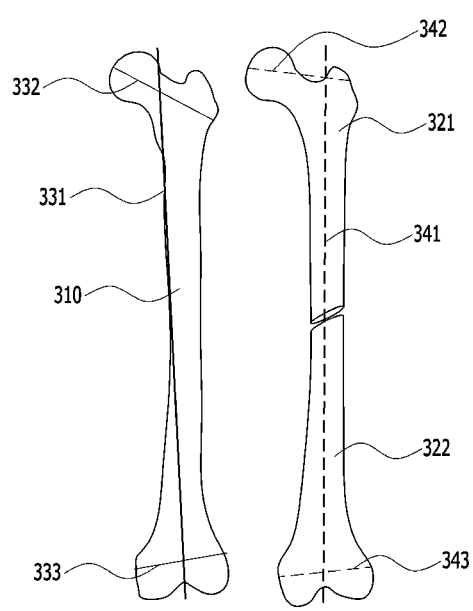
FIG. 3 is a view showing a first model of a broken bone, a second model assumed to be obtained after restoration, and spatial axis information obtained via markers to match the first and second models with each other as one process of a computer assistance method for the reduction of a fracture according to an embodiment of the present invention.

FIG. 3 is a view showing a first model of a broken bone, a second model 310 assumed to be obtained after restoration, and spatial axis information obtained via markers to match the first and second models with each other as one process of a computer assistance method for the reduction of a fracture according to an embodiment of the present invention.

In FIG. 3, a 3D model of the broken bone is presented. When the 3D model of the broken bone is referred to as the first model for ease of description, the proximal part 321 and distal part 322 of the first model are shown. The second model 310 assumed to be obtained after the restoration of the broken bone attributable to a reduction operation is also shown.

The second model 310 may be acquired through the mirroring transformation of the unbroken whole bone. Since opposite legs form bilateral symmetry, the above-described technique is a technique using this characteristic. It will be apparent that there is a case where it is not easy to use the opposite leg. In this case, the second model 310 may be acquired using a plan for an operation on the broken bone, reconstruction using the 3D model of the broken bone, a standardized anatomical model of a specific body region obtained using characteristic information, such as the age, gender, and/or the like of a patient, and/or the like.

In order to practice the present invention, a plurality of reference markers is attached to a bone in order to perform motion tracking during an operation, and variations in the location and orientation of the bone actually made during the operation, i.e., spatial information, are received from/via the markers. The received spatial information of the markers represents exactly the spatial information of the bone. There is acquired a real-time 3D model (a third model in the present specification), in which spatial information has been updated in the state of being registered onto a surgical navigation space recognizable by a surgical navigation system by incorporating the received spatial information into the 3D model of the bone. The markers are tracked using the real-time 3D model. Since the markers have three spatial axes, they may transfer not only accurate location information but also accurate orientation information regarding tilting, yawing, etc.

In order to enable more accurate comparison, when a pre-operative image used to generate a 3D model is acquired, it may be possible to attach markers and generate a 3D model to which the location and orientation information of the markers have been added.

In FIG. 3, there is shown an example of an image indicating the orientation information of the first model 321 and 322 and the second model 310 when such markers are used. The second model 310 is shown to include the central axis 331, second axis 332, and third axis 333 of the bone. The central axis 331 represents the long axis of a bone shaft, the second axis 332 represents a long axis including the femur head and neck of the proximal part of the second model 310, and the third axis 333 represents a transepicondylar axis (TEA) connecting two protrusions, i.e., a lateral epicondyle and a medial epicondyle, of the distal part of the second model 310.

The angle formed by the second axis 332 and the third axis 333 is maintained at an angle formed in an anatomical bone model of a normal human body. In the case where the second model 310 is obtained by mirroring the 3D model of the unbroken whole bone, the second axis 332 and the third axis 333 inside the second model 310 naturally form an angle in an anatomical bone model of a normal human body. The angle in an anatomical bone model of a normal human may be presented by a specific angle range by means of statistics indices, such as an average value and a standard deviation. In the case where the second model 310 is obtained using a standardized model of a bone of a human body, the angle formed by the second axis 332 and the third axis 333 inside the second model 310 may also follow that of an anatomical bone model of a normal human body.

The first model 321 and 322 is shown along with information about three spatial axes. In the first model 321 and 322 in which the proximal part 321 and the distal part 322 are spaced apart from each other, reduction needs to be performed such that the angle formed by the fourth axis 342 of the proximal part 321 and the fifth axis 343 of the distal part 322 follows that of the anatomical bone model of the normal human body. In order to perform reduction, it is required that the angle between the fourth axis 342 of the proximal part 321, i.e., a long axis including the femur head and the neck, and the fifth axis 343 of the distal part 322, i.e., a TEA, should be maintained within a common range of angles formed in the anatomical bone model of the normal human body. This process may be performed through, for example, the registration between the first model 321 and 322 and the second model 310.

In this case, a central axis 341 for the first model 321 and 322 may be set based on the proximal part 321 for the sake of convenience. In an embodiment, the central axis 341 for the proximal part 321 and a central axis for the distal part 322 may be separately shown. In FIG. 3, there is shown a case where the reduction of the distal part 322 and the proximal part 321 is incomplete but the alignment between the central axis of the proximal part 321 and the central axis of the distal part 322 is achieved, so that the central axis of the distal part 322 is substantially aligned with the central axis 341 of the proximal part 321 and thus the incomplete reduction is not prominently shown in the image. Although the three axes 341, 342 and 343 of the first model 321 and 322 are not necessarily aligned with the three axes 331, 332 and 333 of the second model 310, the process of adjusting the angle formed by the fourth axis 342 and fifth axis 343 of the first model 321 and 322 within a standardized angle range represented by a bone model of a normal human body may be performed as part of a reduction process.

When the orientations of the proximal part 321 and the distal part 322 have been aligned with each other through the process of aligning or reducing the three axes of the proximal part 321 of the broken bone and the three axes of the distal part 322 of the broken bone in FIG. 3, there may be performed the process of coapting/joining the proximal part 321 and the distal part 322 while checking the current progress of reduction against the second model 310, i.e., a final treatment target. The subsequent process will be described with reference to FIG. 4.

Figure 4:
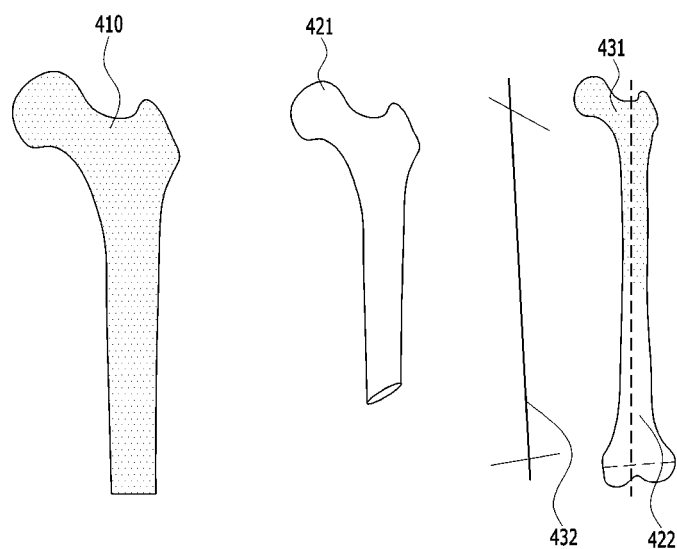
FIG. 4 is a view showing the distal part of the first model of the broken bone and the overlay information of the second model as one process of the computer assistance method for the reduction of a fracture according to the embodiment of the present invention.
Figure 5:
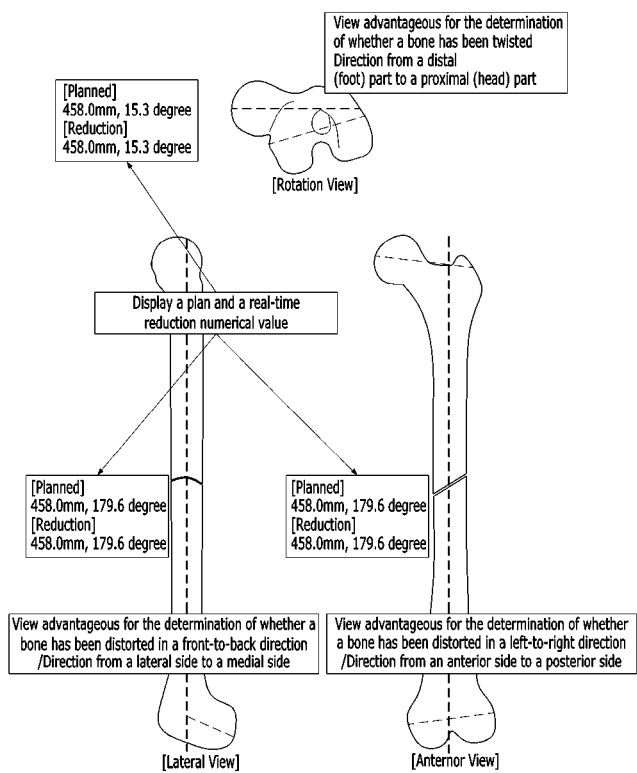
FIG. 5 is a view showing a rotation view, a lateral view, and an anterior view as an example of overlay information displayed in an embodiment of the present invention.

FIG. 4 is a view showing the distal part of the first model of the broken bone and the overlay information of the second model as one process of the computer assistance method for the reduction of a fracture according to the embodiment of the present invention. The first models shown in FIGS. 4 and 5 may be understood as being all replaced with third models when spatial information is updated through real-time marker tracking. FIGS. 4 and 5 may be understood showing first models in which spatial information is not updated yet at a pre-operative preparation step. Alternatively, FIGS. 4 and 5 may be understood showing third models in which spatial information has been updated. The following description is valid for any one of the cases (for first model or third model). FIG. 4 shows a second model 410, the proximal part 421 of a first model, the distal part 422 of the first model, and a second model 431 overlaid on the distal part 422 of the first model.

First, the second model 410 is registered with the proximal part 421 of the first model. The model obtained by replacing with and overlaying the second model 410 registered with the proximal part 421 of the first model on the real-time image of the first model 321 and 322 of FIG. 3 may be the overlaid second model 431 of FIG. 4. In this case, it may be verified again whether the orientation of the distal part 422 of the first model is twisted with respect to the outline of the overlaid second model 431 and whether the distal part 422 of the first model is spaced apart from the proximal part 421 by a reference value or larger.

Depending on the progress of an operation, the image of FIG. 3 may be replaced with the image of FIG. 4. When necessary, both the image of FIG. 3 and the image of FIG. 4 may be displayed on the same screen.

In any case, in the case of the first model, a 3D model is extracted and displayed based on an actually photographed real-time image. In order to display the 3D model from the real-time 2D image, it is advantageous to additionally visualize orientation information regarding three axes used in the process of registering the 3D model.

Through this process, the present invention can visually display planned reduction reference information and provide intuitiveness by simultaneously overlaying and providing the outline of the second model assumed to be obtained after restoration and the outline of the first model of the bone during an operation.

In this case, although it can be determined whether a current state is a twisted state through the simple, simultaneous display of 3D models, there may be required additional information about the direction in which force is applied to move the bone and about the magnitude of the force.

This additional information is provided along with various views intuitively perceivable by a user, and thus the present invention may intuitively transfer more precise and detailed information to the user.

FIG. 5 is a view showing a rotation view, a lateral view, and an anterior view as an example of overlay information displayed in an embodiment of the present invention.

The rotation view shown in FIG. 5 is a view obtained by viewing a 3D model of a broken bone along its central axis. The rotation view shown in FIG. 5 is a view obtained by viewing the model in the direction from the distal part Foot to the proximal part Head. In an embodiment, a rotation view obtained by viewing the model from the proximal part to the distal part may be displayed, or two rotation views obtained by viewing the model in opposite directions may be displayed together.

A rotation view provides information which is considerably intuitive and advantageous for the determination of whether a bone has been twisted. A rotation view obtained by viewing the bone from a proximal part to a distal part may transfer detailed information about the proximal part, i.e., a reference for reduction, and locations and orientations are fixed in the view. A rotation view obtained by viewing a bone from a distal part to a proximal part is used to adjust a location and a rotating axis with respect to the proximal part through translation and rotation.

A lateral view provides information which is intuitive and advantageous for the determination of whether a bone has been distorted in a front-to-back direction. A lateral view obtained by viewing a bone from a lateral side to a medial side may be displayed with first and second models overlaid on each other. The target angle of the second model based on an operation plan (a simulation), the degree of spacing between the proximal and distal parts of the first model currently in progress, an angle formed by the central axis of the first model, etc. may be displayed as additional information. Accordingly, the progress of registration and reduction and information about whether reduction is maintained during an operation process when the reduction has been performed may be determined via the numerical values. In an embodiment, the degree of spacing may be directly displayed, and the target length of a reduced bone and the length of a central axis formed by proximal and distal parts based on the status of an operation currently in progress may be displayed. Accordingly, information may be provided such that the degree of spacing may be inferred from the comparison of the information.

An anterior view is a view obtained by viewing a bone from an anterior side to a posterior side. An anterior view provides information which is efficient and intuitive for the determination of whether a bone has been distorted in a left-to-right direction.

Numerical values displayed during an operation process may include the following numerical values:

There may be displayed the length (measured along a central axis) of a reduced bone at a plan establishment step, an internal angle formed by the axis of a proximal part (a head part) and the axis of a distal part (a bottom part) at the plan establishment step, the length of a bone reduced and in coaptation at an actual operation step, and an internal angle formed by the axis of the proximal part and the axis of the distal part at the actual operation step.

A numerical value displayed along with a lateral view or anterior view may be an internal/interior angle which is formed by the axis of a proximal part and the axis of a distal part on the reference plane of the view.

Furthermore, depending on the progress of an operation, a specific view may be enlarged and then displayed. This process may be sequentially applied in conjunction with a previously established operation plan. For example, when it is determined whether a bone has been twisted first, a rotation view may be enlarged and provide support such that the twisting of the bone can be precisely corrected. Thereafter, a lateral view may be enlarged and checked for front-to-back distortion, and an anterior view may be enlarged and checked for left-to-right distortion.

When orientations have been adjusted, an image enlarged around a coaptation target region (a fracture region) may be displayed in order to minimize spacing in the coaptation target region.

Figure 6:
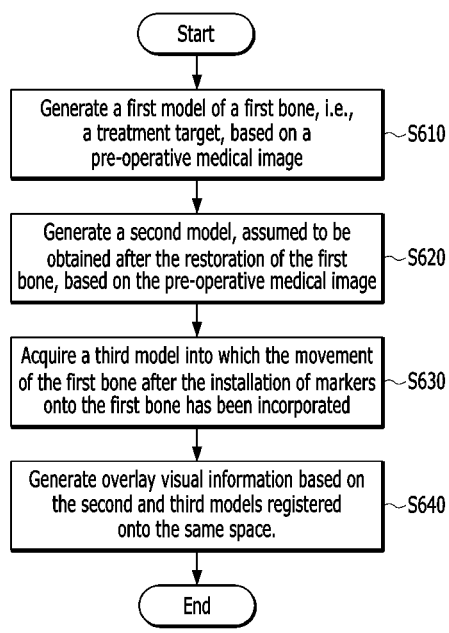
FIG. 6 is an operation flowchart showing a computer assistance method for the reduction of a fracture according to an embodiment of the present invention.

FIG. 6 is an operation flowchart showing a computer assistance method for the reduction of a fracture according to an embodiment of the present invention.

Referring to FIG. 6, a computer assistance system/computing system according to the present invention may generate a first model of a first bone, i.e., a treatment target, based on a pre-operative medical image at step S610.

At step S620, the computing system may generate a second model, assumed to be obtained after the restoration of the first bone, based on the pre-operative medical image.

At step S630, the computing system may acquire a third model in which the spatial information of the first model has been updated by incorporating, into the spatial information, the movement of the first bone occurring during treatment after the installation of markers onto the first bone. It will be apparent that the installation of markers is not limited to the third model. When the pre-operative medical image is acquired, markers may be also installed and utilized.

At step S640, the computing system may generate overlay visual information based on the second model for the first bone represented via the third model. The overlay visual information may be sequential variations in the layout of the screen or the like based on the progress of the operation. The progress of the operation is checked against a previously established operation plan, and switching between screens may be intentionally promoted or delayed by a user via a button or the like added to a surgical navigation system.

A computer assistance method for the reduction of a fracture according to an embodiment of the present invention may be implemented in the form of program instructions which can be executed by a variety of computer means, and may be stored in a computer-readable storage medium. The computer-readable storage medium may include program instructions, a data file, and a data structure solely or in combination. The program instructions which are stored in the medium may be designed and constructed particularly for the present invention, or may be known and available to those skilled in the field of computer software. Examples of the computer-readable storage medium include magnetic media such as a hard disk, a floppy disk and a magnetic tape, optical media such as CD-ROM and a DVD, magneto-optical media such as a floptical disk, and hardware devices particularly configured to store and execute program instructions such as ROM, RAM, and flash memory. Examples of the program instructions include not only machine language code which is constructed by a compiler but also high-level language code which can be executed by a computer using an interpreter or the like. The above-described hardware components may be configured to act as one or more software modules which perform the operation of the present invention, and vice versa.

However, the present invention is not limited and restricted by the embodiments. Throughout the drawings, the same reference symbols denote the same members. The lengths, heights, sizes, widths, etc. introduced in the embodiments and drawings of the present invention may be exaggerated to help an understanding of the present invention.

According to the present invention, the registration between medical images can not only be improved efficiently, but an improved user interface for guidance on an operation can be also implemented such that a user can clearly become aware of the accurate relative locations, orientations, and alignment of the proximal and distal parts of a broken bone.

According to the present invention, there can be provided guidance which is configured to generate a 3D model of a fractured bone from a previously photographed pre-operative image, to register and compare the spatial information of the fractured bone acquired in real time in connection with markers with the existing 3D model, and to provide views of the 3D model in various directions, thereby enabling the accurate reduction of the fractured bone without twisting as well as dislocation and spacing.

According to the present invention, there can be implemented user guidance which is capable of improving the completeness of a current operation by using a 3D model using a previously generated pre-operative image and a real-time 3D model in which spatial information has been updated at a site where an operation for the reduction of a fracture is performed using a surgical navigation system, etc.

According to the present invention, there can be implemented a user interface which is capable of constructing a workflow through the image processing of medical images, comparing a 3D model with a 3D model in which current real-time spatial information has been updated through the workflow, and more effectively transferring the results of the comparison to a user (an operator).

Furthermore, the computer assistance method for the image-guided reduction of a fracture which can be implemented according to the present invention can be more effectively used in an operation for the reduction of a fracture which is automated via a robot. A user interface implemented according to the present invention is overlaid on an image on a monitor which is viewed by an operator in order to control a surgical navigation system or is displayed along with the image for simultaneous reference, thereby reducing an operation process and errors.

According to the present invention, there can be provided a 3D model in which real-time spatial information has been updated through location tracking and synchronization regarding markers attached to a leg of a patient without actually photographing/imaging a radiographic or ultrasonic image during an operation, thereby providing intuitive and efficient guidance and an intuitive and efficient user interface to a user (an operator).

The present invention was derived from the research conducted as part of the Industrial Convergence-based Fundamental Technology Development Project sponsored by the Korean Ministry of Trade, Industry and Energy and the Korea Evaluation Institute of Industrial Technology [Project Management Number: 10041605; and Project Name: Development of 2 mm Error-level Bone Positioning and Tunneling Surgery Robot System for Improvement of Accuracy and Safety of Damaged Upper and Lower Limb Muscle Recovery Operation].

While the present invention has been described in conjunction with specific details, such as specific elements, and the limited embodiments and diagrams above, these are provided merely to help an overall understanding of the present invention. The present invention is not limited to these embodiments, and various modifications and alterations may be made based on the foregoing description by a person having ordinary knowledge in the art to which the present invention pertains.

Therefore, the technical spirit of the present invention should not be determined based on only the described embodiments, and the following claims, all equivalents to the claims and equivalent modifications should be construed as falling within the scope of the spirit of the present invention.

What is claimed is:

1. A computer assistance method for reduction of a fracture, the method comprising:
   generating a first model of a first bone, which is a treatment target, based on a pre-operative medical image;
   generating a second model, assumed to be obtained after restoration of the first bone, based on the pre-operative medical image;
   acquiring a third model in which spatial information of the first model has been updated by incorporating, into the spatial information, movement of the first bone occurring during treatment after installation of markers onto the first bone; and
   generating overlay visual information based on the second and third models registered onto a same space,
   wherein the generating the overlay visual information comprises:
   extracting a first central axis of the first bone and a second central axis of the second model; and
   generating the overlay visual information such that the second central axis is displayed for a portion where the first bone is missing by matching the first central axis of the first bone with the second central axis of the second model.

2. The computer assistance method of claim 1, wherein the generating overlay visual information comprises:
   matching an outline of the first bone represented by the third model with a first portion of an outline of the second model; and
   generating the overlay visual information such that a second portion of the outline of the second model, which is a remainder of the outline of the second model, is connected to the outline of the first bone.

3. The computer assistance method of claim 1, further comprising displaying a proximal segment of the first bone, a distal segment of the first bone, and the overlay visual information together; and
   wherein the overlay information is generated for the proximal segment of the first bone, and wherein the overlay information guides a location of the distal segment relative to the proximal segment.

4. The computer assistance method of claim 1, wherein the overlay visual information comprises:
   visual information indicating a distance between a proximal segment of the first bone and a distal segment of the first bone; and
   visual information indicating whether orientations of central axis of the proximal segment and central axis of the distal segment match each other.

5. The computer assistance method of claim 1, further comprising providing one or more of a rotation view, a lateral view, and an anterior view for the third model; and
   wherein the overlay visual information is generated based on the second model for each of the one or more views provided for the third model.

6. The computer assistance method of claim 1, wherein the second model is generated through symmetric transformation of a second bone located opposite to the first bone.

7. A computing system for assisting reduction of a fracture, the system comprising a processor and being connected to a display device; wherein the processor configured to:
   generate a first model of a first bone, which is a treatment target, based on a pre-operative medical image;
   generate a second model, assumed to be obtained after restoration of the first bone, based on the pre-operative medical image;
   acquire spatial information of the first model which has been updated by incorporating, into the spatial information, movement of the first bone occurring during treatment after installation of markers onto the first bone;
   generate a third model based on the updated spatial information of the first model;
   extract a first central axis of the first bone and a second central axis of the second model; and
   generate overlay visual information based on the second and third models registered onto a same space such that the second central axis is displayed for a portion where the first bone is missing by matching the first central axis of the first bone with the second central axis of the second model.

8. The computing system of claim 7, wherein the processor is further configured to:
   match an outline of the first bone represented by the third model with a first portion of an outline of the second model; and
   generate the overlay visual information such that a second portion of the outline of the second model, which is a remainder of the outline of the second model, is connected to the outline of the first bone.

9. The computing system of claim 7, wherein the processor is further configured to:
   generate display information for a proximal segment of the first bone and a distal segment of the first bone to be displayed along with the overlay visual information; and
   generate the overlay visual information for the proximal segment of the first bone such that the overlay visual information guides a location of the distal segment relative to the proximal segment.

10. The computing system of claim 7, wherein the overlay visual information comprises:
    visual information indicating a distance between a proximal segment of the first bone and a distal segment of the first bone; and
    visual information indicating whether orientations of central axis of the proximal segment and central axis of the distal segment match each other.

11. The computing system of claim 7, wherein the processor is further configured to:
    provide one or more of a rotation view, a lateral view, and an anterior view for the third model; and
    generate the overlay visual information based on the second model for each of the one or more views provided for the third model.

12. A non-transitory computer-readable medium containing program instructions executed by a processor installed in a computing system for assisting reduction of a fracture, wherein the program instructions comprising:
    program instructions generate a first model of a first bone, which is a treatment target, based on a pre-operative medical image;
    program instructions generate a second model, assumed to be obtained after restoration of the first bone, based on the pre-operative medical image;
    program instructions acquire spatial information of the first model which has been updated by incorporating, into the spatial information, movement of the first bone occurring during treatment after installation of markers onto the first bone;
    program instructions generate a third model based on the updated spatial information of the first model;
    program instructions extract a first central axis of the first bone and a second central axis of the second model; and
    program instructions generate overlay visual information based on the second and third models registered onto a same space such that the second central axis is displayed for a portion where the first bone is missing by matching the first central axis of the first bone with the second central axis of the second model.

* * * * *